US011246814B2

(12) United States Patent
Agach et al.

(10) Patent No.: US 11,246,814 B2
(45) Date of Patent: Feb. 15, 2022

(54) OXIDIZING COMPOSITION FOR TREATING KERATIN MATERIALS, COMPRISING A FATTY SUBSTANCE AND OXYALKYLENATED SURFACTANTS

(71) Applicant: L'OREAL, Paris (FR)

(72) Inventors: Mickaël Agach, Saint-Ouen (FR); Maxime Pourret, Saint-Ouen (FR); Leila Hercouet, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/061,911

(22) PCT Filed: Dec. 19, 2016

(86) PCT No.: PCT/EP2016/081710
§ 371 (c)(1),
(2) Date: Jun. 13, 2018

(87) PCT Pub. No.: WO2017/103260
PCT Pub. Date: Jun. 22, 2017

(65) Prior Publication Data
US 2018/0369096 A1 Dec. 27, 2018

(30) Foreign Application Priority Data

Dec. 18, 2015 (FR) ........................................ 1562818
Dec. 18, 2015 (FR) ........................................ 1562832

(51) Int. Cl.
| | | |
|---|---|---|
| *A61K 8/39* | (2006.01) |
| *A61K 8/31* | (2006.01) |
| *A61K 8/37* | (2006.01) |
| *A61K 8/41* | (2006.01) |
| *A61K 8/92* | (2006.01) |
| *A61Q 5/04* | (2006.01) |
| *A61Q 5/06* | (2006.01) |
| *A61Q 5/08* | (2006.01) |
| *A61Q 5/10* | (2006.01) |
| *A61K 8/86* | (2006.01) |

(52) U.S. Cl.
CPC ............... *A61K 8/39* (2013.01); *A61K 8/31* (2013.01); *A61K 8/37* (2013.01); *A61K 8/41* (2013.01); *A61K 8/86* (2013.01); *A61K 8/922* (2013.01); *A61K 8/925* (2013.01); *A61Q 5/04* (2013.01); *A61Q 5/065* (2013.01); *A61Q 5/08* (2013.01); *A61Q 5/10* (2013.01); *A61K 2800/4322* (2013.01); *A61K 2800/4324* (2013.01)

(58) Field of Classification Search
None
See application file for complete search history.

(56) References Cited

U.S. PATENT DOCUMENTS

| 4,003,699 | A | 1/1977 | Rose et al. |
|---|---|---|---|
| RE30,199 | E | 1/1980 | Rose et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Mockli |
| 5,766,576 | A | 6/1998 | Lowe et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,730,789 | B1 | 5/2004 | Birault et al. |
| 6,884,265 | B2 | 4/2005 | Vidal et al. |
| 7,060,110 | B2 | 6/2006 | Vidal et al. |
| 2002/0095732 | A1 | 7/2002 | Kravtchenko et al. |
| 2003/0106169 | A1 | 6/2003 | Vidal et al. |
| 2004/0093675 | A1 | 5/2004 | Vidal et al. |
| 2004/0107513 | A1 | 6/2004 | Vidal et al. |
| 2004/0127692 | A1 | 7/2004 | David et al. |

(Continued)

FOREIGN PATENT DOCUMENTS

| DE | 2359399 A1 | 6/1975 |
|---|---|---|
| DE | 3843892 A1 | 6/1990 |

(Continued)

OTHER PUBLICATIONS

International Search Report for Application No. PCT/EP2016/081710, dated Feb. 8, 2017.

*Primary Examiner* — Dominic Lazaro
(74) *Attorney, Agent, or Firm* — The Marbury Law Group, PLLC

(57) ABSTRACT

The present invention relates to a composition for treating keratin materials, in particular keratin fibres, and in particular human keratin fibres such as the hair, comprising, in a cosmetically acceptable medium: at least one fatty substance in a content of greater than or equal to 10% by weight relative to the total weight of the composition, at least one oxyalkylenated (OA), preferably oxyethylenated (OE), nonionic surfactant comprising a number of OA units, preferably OE units, ranging from 1 to 9, at least one oxyalkylenated (OA), preferably oxyethylenated (OE), nonionic surfactant comprising at least 10 OA units, preferably OE units, the weight ratio of the amount of oxyalkylenated (OA), preferably oxyethylenated, nonionic surfactant(s) comprising a number of OA units, preferably OE units, ranging from 1 to 9 to the amount of oxyalkylenated (OA), preferably oxyethylenated, nonionic surfactants comprising at least 10 OA units, preferably OE units, being greater than 1, at least one chemical oxidizing agent, preferably hydrogen peroxide. The composition in accordance with the invention may be used for dyeing, bleaching or permanently reshaping keratin materials, in particular keratin fibres. It produces ready-to-use compositions that give good dyeing, bleaching or permanent-reshaping properties without degrading the keratin materials, in particular keratin fibres, and without impairing their cosmetic properties.

20 Claims, No Drawings

(56) References Cited

U.S. PATENT DOCUMENTS

| | | |
|---|---|---|
| 2004/0143911 A1 | 7/2004 | Vidal |
| 2004/0168263 A1 | 9/2004 | Vidal |
| 2004/0200009 A1 | 10/2004 | Vidal |
| 2004/0244123 A1 | 12/2004 | Vidal et al. |
| 2005/0039268 A1 | 2/2005 | Plos et al. |
| 2014/0068876 A1* | 3/2014 | Rapold ............... A61K 8/062 8/406 |

FOREIGN PATENT DOCUMENTS

| | | | |
|---|---|---|---|
| DE | 4133957 A1 | 4/1993 | |
| DE | 19543988 A1 | 5/1997 | |
| EP | 0714954 A2 | 6/1996 | |
| EP | 0770375 A1 | 5/1997 | |
| FR | 2733749 A1 | 11/1996 | |
| FR | 2750048 A1 | 12/1997 | |
| FR | 2801308 A1 | 5/2001 | |
| FR | 2807650 A1 | 10/2001 | |
| FR | 2822693 A1 | 10/2002 | |
| FR | 2822694 A1 | 10/2002 | |
| FR | 2822696 A1 | 10/2002 | |
| FR | 2822698 A1 | 10/2002 | |
| FR | 2825625 A1 | 12/2002 | |
| FR | 2825702 A1 | 12/2002 | |
| FR | 2829926 A1 | 3/2003 | |
| FR | 2844269 A1 | 3/2004 | |
| FR | 2886136 A1 | 12/2006 | |
| FR | 2970176 A1 | 7/2012 | |
| FR | 2974503 A1 | 11/2012 | |
| FR | 2984737 A1 | 6/2013 | |
| FR | 3015274 A1 | 6/2015 | |
| GB | 1026978 A | 4/1966 | |
| GB | 1153196 A | 5/1969 | |
| JP | 02-019576 A | 1/1990 | |
| JP | 05-163124 A | 6/1993 | |
| WO | 94/08969 A1 | 4/1994 | |
| WO | 94/08970 A1 | 4/1994 | |
| WO | 95/01772 A1 | 1/1995 | |
| WO | 95/15144 A1 | 6/1995 | |
| WO | 96/15765 A1 | 5/1996 | |
| WO | 02/078660 A1 | 10/2002 | |
| WO | 02/100369 A2 | 12/2002 | |
| WO | 02/100834 A1 | 12/2002 | |
| WO | 2012095395 A2 | 7/2012 | |
| WO | WO 2013/069168 * | 5/2013 | |
| WO | 2015007915 A1 | 1/2015 | |
| WO | WO-2015007915 A1 * | 1/2015 | ............... A61Q 5/10 |

* cited by examiner

OXIDIZING COMPOSITION FOR TREATING KERATIN MATERIALS, COMPRISING A FATTY SUBSTANCE AND OXYALKYLENATED SURFACTANTS

CROSS REFERENCE TO RELATED APPLICATIONS

This is a national stage application of PCT/EP2016/081710, filed internationally on Dec. 19, 2016, which claims priority to French Applications No. 1562818 and No. 1562832, both filed on Dec. 18, 2015, all of which are incorporated by reference herein in their entireties.

The present invention relates to a composition for treating keratin materials, and in particular human keratin fibres such as the hair, comprising, in a cosmetically acceptable medium, a fatty substance in a content of greater than or equal to 10% by weight, an oxyalkylenated (OA), preferably oxyethylenated (OE), nonionic surfactant comprising a number of oxyalkylene units ranging from 1 to 9, and an oxyalkylenated (OA), preferably oxyethylenated (OE), nonionic surfactant comprising at least 10 oxyalkylene units, in a defined ratio, and a chemical oxidizing agent.

In cosmetics, oxidizing compositions are used in the fields of dyeing, bleaching and permanently transforming or reshaping keratin fibres, and in particular human keratin fibres such as the hair.

Thus, in the oxidation dyeing of hair, oxidizing compositions are mixed with oxidation dyes (bases and couplers), which are colourless in themselves, to generate compounds that are coloured and colouring by a process of oxidative condensation. Oxidizing compositions are also used in the direct dyeing of the hair as a mixture with certain direct dyes that are coloured and colouring, in order to obtain a colouring with a lightening effect on the hair. Among the oxidizing agents conventionally used for dyeing keratin fibres, mention may be made of hydrogen peroxide or compounds that are capable of producing hydrogen peroxide by hydrolysis, such as urea peroxide. Persalts such as perborates and persulfates may also be used. Hydrogen peroxide is more particularly preferred.

In hair bleaching, bleaching compositions contain one or more oxidizing agents. Among these oxidizing agents, the ones most conventionally used are hydrogen peroxide or compounds that are capable of producing hydrogen peroxide by hydrolysis, such as urea peroxide or persalts such as perborates, percarbonates and persulfates, hydrogen peroxide and persulfates being particularly preferred.

These compositions may be aqueous compositions containing alkaline agents (amines or aqueous ammonia) that are diluted at the time of use with an aqueous hydrogen peroxide composition.

These compositions may also be formed from anhydrous products that contain alkaline compounds (amines and/or alkaline silicates), and a peroxygenated reagent such as ammonium or alkali metal persulfates, perborates or percarbonates, which is diluted at the time of use with an aqueous hydrogen peroxide composition.

Permanently reshaping the hair consists, in a first step, in opening the —S—S-disulfide bonds of keratin (cystine) using a composition containing a suitable reducing agent (reduction step), and then, after having rinsed the head of hair thus treated, in reconstituting the disulfide bonds, in a second step, by applying to the hair, which has been placed under tension beforehand (curlers and others), an oxidizing composition (oxidation step, also known as the fixing step) so as finally to give the hair the desired shape. This technique thus makes it possible, without preference, either to make the hair wavy or to relax or uncurl it. The new shape given to the hair by a chemical treatment such as that above is eminently long-lasting and especially withstands washing with water or shampoos, as opposed to the simple standard techniques of temporary reshaping, such as hairsetting.

The oxidizing compositions required for performing the fixing step are usually compositions based on aqueous hydrogen peroxide solution. It is sought to obtain compositions that are ever more effective, in particular in terms of lightening or bleaching, while respecting as far as possible the integrity of the keratin fibres and giving said fibres the best possible cosmetic properties.

To do this, oil-rich oxidizing compositions have been proposed, in emulsion form, but incorporating high oil contents may cause the emulsion to destabilize.

Moreover, in the cosmetic field, it is always sought to improve the conditioning of the hair, that is to say especially to improve the properties of smoothness and softness of feel.

The compositions obtained must also have good mixing and application properties, and especially good rheological properties so as not to run down the face, onto the scalp or beyond the areas that it is proposed to treat, when they are applied.

The aim of the present invention is to provide novel oxidizing compositions that can improve the cosmetic properties of keratin materials, in particular of keratin fibres such as the hair and that are stable over time.

This aim is achieved with the present invention, one subject of which is a composition for treating keratin materials, and in particular the hair, comprising, in a cosmetically acceptable medium:
  at least one fatty substance, which is preferably liquid, in a content of greater than or equal to 10% by weight relative to the total weight of the composition,
  at least one oxyalkylenated (OA), preferably oxyethylenated (OE), nonionic surfactant comprising a number of OA units, preferably OE units, ranging from 1 to 9,
  at least one oxyalkylenated (OA), preferably oxyethylenated (OE), nonionic surfactant comprising at least 10 OA units, preferably OE units,
the weight ratio of the amount of oxyalkylenated nonionic surfactant(s) comprising a number of OA units ranging from 1 to 9 to the amount of oxyalkylenated nonionic surfactants comprising at least 10 OA units being greater than 1,
said oxyalkylenated nonionic surfactant(s) comprising a number of OA units ranging from 1 to 9 and said oxyalkylenated nonionic surfactants comprising at least 10 OA units being chosen from saturated or unsaturated, linear or branched oxyethylenated $C_8$-$C_{30}$ fatty alcohols,
  at least one chemical oxidizing agent, preferably hydrogen peroxide.

According to the invention, the term "chemical oxidizing agent" means an oxidizing agent other than atmospheric oxygen.

When the composition in accordance with the invention is used for dyeing keratin fibres, good dyeing properties are obtained, especially strong, powerful, chromatic and sparingly selective colourings that allow good coverage of grey hair and that show good resistance to the various attacking factors to which the hair may be subjected, such as shampoo, light, sweat and permanent reshaping operations, without impairing the cosmetic properties of the keratin fibres.

When the composition in accordance with the present invention is used for bleaching or lightening keratin materials, especially the skin or keratin fibres, it produces a good lightening effect on the keratin materials without degrading them or impairing their cosmetic properties.

When the composition in accordance with the present invention is used for permanently reshaping keratin fibres, it produces satisfactory permanent reshaping of these fibres without degrading them and without impairing their cosmetic properties.

Furthermore, the composition in accordance with the invention shows good stability over time, especially on storage at high temperatures, for example of about 45° C.

A subject of the invention is also a process for treating keratin materials, in particular keratin fibres, especially a process for dyeing, bleaching (or lightening) or permanently reshaping keratin materials, in particular keratin fibres, using this oxidizing composition.

Another subject of the invention is the use of this oxidizing composition for treating keratin materials, in particular keratin fibres, especially for dyeing, bleaching or permanently reshaping keratin materials, in particular keratin fibres.

In the text hereinbelow, unless otherwise indicated, the limits of the indicated ranges are included in the invention.

The term "at least one" means "one or more".

Oxyalkylenated Surfactants

The composition according to the invention comprises at least one oxyalkylenated (OA) nonionic surfactant comprising a number of OA units ranging from 1 to 9 and at least one oxyalkylenated (OA) nonionic surfactant comprising at least 10 OA units chosen from saturated or unsaturated, linear or branched oxyethylenated $C_8$-$C_{30}$ fatty alcohols.

The weight ratio, in the composition of the invention, of the amount of oxyalkylenated nonionic surfactant(s) comprising a number of OA units ranging from 1 to 9 to the amount of oxyalkylenated nonionic surfactant(s) comprising at least 10 OA units is greater than 1, preferably greater than or equal to 1.2, better still greater than or equal to 1.5 and even better still greater than or equal to 2.

This weight ratio may range, for example, from 1.2 to 15, better still from 1.5 to 10 and even better still from 2 to 5.

Preferably, the oxyalkylenated nonionic surfactant(s) comprising at least 10 OA units, preferably OE units, and the oxyalkylenated nonionic surfactant(s) comprising from 1 to 9 OA units, preferably OE units, are chosen from saturated or unsaturated, linear or branched, preferably linear, $C_{12}$-$C_{22}$, better still $C_{14}$-$C_{20}$, oxyethylenated fatty alcohols, for instance cetyl alcohol, oleyl alcohol, oleocetyl alcohol, behenyl alcohol, cetearyl alcohol and stearyl alcohol, and mixtures thereof, and more preferably stearyl alcohol. Preferably, the oxyethylenated nonionic surfactant comprising at least 10 OE units and the oxyethylenated nonionic surfactant comprising from 1 to 9 OE units are chosen from oxyethylenated, saturated or unsaturated, linear or branched, preferably linear, $C_8$-$C_{30}$, preferably $C_{12}$-$C_{22}$ and better still $C_{14}$-$C_{20}$, fatty alcohols, for instance cetyl alcohol, oleyl alcohol, oleocetyl alcohol, behenyl alcohol, cetearyl alcohol and stearyl alcohol, and mixtures thereof, and more preferably stearyl alcohol.

Use is preferably made, as oxyalkylenated, preferably oxyethylenated, nonionic surfactant comprising from 1 to 9 OA units, preferably OE units, of oxyalkylenated, preferably oxyethylenated, nonionic surfactants comprising from 2 to 8 and preferably from 2 to 4 OA units, preferably OE units, for instance the products of addition of ethylene oxide and stearyl alcohol such as stearyl alcohol 2 OE (CTFA name: Steareth-2).

The oxyalkylenated, preferably oxyethylenated, nonionic surfactants comprising at least 10 OA units, preferably OE units, used in the invention may especially contain a number of oxyalkylene groups, preferably oxyethylene groups, ranging from 10 to 50, preferably from 15 to 30 and better still from 15 to 25, for instance the products of addition of ethylene oxide and stearyl alcohol such as stearyl alcohol 20 OE (CTFA name: Steareth-20).

The content of oxyalkylenated, preferably oxyethylenated, nonionic surfactant(s) comprising from 1 to 9 oxyalkylene units, preferably oxyethylene units, chosen from saturated or unsaturated, linear or branched oxyethylenated $C_8$-$C_{30}$ fatty alcohols, in the composition according to the invention may range from 0.5% to 15% by weight, preferably from 1% to 10% by weight and better still from 2% to 6% by weight relative to the total weight of the composition.

The content of oxyalkylenated, preferably oxyethylenated, nonionic surfactants comprising at least 10 oxyalkylene groups, preferably oxyethylene groups, chosen from saturated or unsaturated, linear or branched oxyethylenated $C_8$-$C_{30}$ fatty alcohols, in the composition according to the invention may range from 0.1% to 15% by weight, preferably from 0.5% to 10% by weight and better still from 1% to 5% by weight relative to the total weight of the composition.

The total amount of oxyalkylenated, preferably oxyethylenated, nonionic surfactants, chosen from saturated or unsaturated, linear or branched oxyethylenated $C_8$-$C_{30}$ fatty alcohols, in the composition may range from 1% to 25% by weight, preferably from 2% to 15% by weight and better still from 3% to 7% by weight relative to the total weight of the composition.

According to one embodiment, the combination of the oxyalkylenated, preferably oxyethylenated, nonionic surfactant(s) comprising at least 10 OA units, preferably OE units, and of the oxyalkylenated, preferably oxyethylenated, nonionic surfactant(s) comprising from 1 to 9 OA units, preferably OE units, chosen from saturated or unsaturated, linear or branched oxyethylenated $C_8$-$C_{30}$ fatty alcohols, constitutes the main surfactant system of the composition.

The term "main surfactant system" means a system which, in its absence, does not lead to the formation of a stable composition.

The term "stable" refers to a composition which, after having been placed in an oven at 45° C. for two months, does not show, after returning to room temperature, any phase separation.

According to a particular embodiment, the combination of the oxyalkylenated, preferably oxyethylenated, nonionic surfactant(s) comprising at least 10 OA units, preferably OE units, and of the oxyalkylenated, preferably oxyethylenated, nonionic surfactant(s) comprising from 1 to 9 OA units, preferably OE units, chosen from saturated or unsaturated, linear or branched oxyethylenated $C_8$-$C_{30}$ fatty alcohols, constitutes the sole surfactant system of the composition.

The term "sole" means that any possible additional surfactant system is present in a content not exceeding 1%, and preferably not exceeding 0.5%. More preferably, the term "sole" denotes a total absence of any other surfactant system.

According to a particular embodiment, the composition comprises a single oxyalkylenated, preferably oxyethylenated, nonionic surfactant comprising at least 10 OA units, preferably OE units, and a single oxyalkylenated, preferably oxyethylenated, nonionic surfactant comprising from 1 to 9 OA units, preferably OE units, as sole surfactant system.

Fatty Substances

The composition according to the invention also comprises one or more fatty substances, which are preferably liquid (or oils).

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

The term "oil" means a "fatty substance" that is liquid at room temperature (25° C.) and at atmospheric pressure (760 mmHg or $1.013 \times 10^5$ Pa).

The term "non-silicone oil" means an oil not containing any silicon (Si) atoms and the term "silicone oil" means an oil containing at least one silicon atom.

More particularly, the fatty substances are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, non-salified fatty acids, esters of fatty acid and/or of fatty alcohol other than triglycerides, non-silicone waxes other than solid fatty alcohols and than solid synthetic esters, and silicones, and mixtures thereof.

It is recalled that, for the purposes of the invention, fatty alcohols, esters and acids more particularly bear at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

The linear or branched hydrocarbons of mineral or synthetic origin, containing more than 16 carbon atoms, are preferably chosen from liquid paraffins, liquid petroleum jelly, polydecenes and hydrogenated polyisobutene such as Parleam®, and mixtures thereof.

As regards the $C_6$-$C_{16}$ lower alkanes, they are linear or branched, or possibly cyclic.

Examples that may be mentioned include hexane, cyclohexane, undecane, dodecane, tridecane or isoparaffins, such as isohexadecane, isodecane or isododecane, and mixtures thereof.

A hydrocarbon-based oil of animal origin that may be mentioned is perhydrosqualene.

The triglycerides of plant or synthetic origin are preferably chosen from liquid fatty acid triglycerides containing from 6 to 30 carbon atoms, for instance heptanoic or octanoic acid triglycerides, or, alternatively, more particularly from those present in plant oils, for instance sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 8 to 30 carbon atoms. Examples that may be mentioned include cetyl alcohol, stearyl alcohol and a mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

The fatty acids that may be used in the context of the invention are more particularly chosen from saturated or unsaturated carboxylic acids containing from 6 to 30 carbon atoms and in particular from 9 to 30 carbon atoms. They are advantageously chosen from myristic acid, palmitic acid, stearic acid, behenic acid, oleic acid, linoleic acid, linolenic acid and isostearic acid. These fatty acids are, in the composition of the invention, not salified with organic or mineral bases, so as not to give rise to soaps.

As regards the esters of fatty acids and/or of fatty alcohols other than the triglycerides mentioned above and plant waxes, mention may be made in particular of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, in particular, oleopalmitate, oleostearate and palmitostearate mixed esters.

More particularly, use is made of monoesters and diesters and in particular sucrose, glucose or methylglucose monooleate or dioleate, stearate, behenate, oleopalmitate, linoleate, linolenate or oleostearate.

An example that may be mentioned is the product sold under the name Glucate® DO by Amerchol, which is a methylglucose dioleate.

Examples of esters or mixtures of esters of sugar and of fatty acid that may also be mentioned include:
- the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% di-tri ester-polyester;
- the sucrose mono-dipalmito-stearate sold by the company Goldschmidt under the name Tegosoft® PSE.

The non-silicone wax(es) other than solid fatty alcohols and solid synthetic esters are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy raw materials that may be used according to the invention are in particular marine waxes, such as the wax sold by the company Sophim under the reference M82, polyethylene waxes or polyolefin waxes in general.

The fatty substance(s) do not comprise any C2-C3 oxyalkylene units. Preferably, they do not contain any glycerol units. More particularly, the fatty substances are other than fatty acids.

More particularly, the fatty substances are chosen from compounds that are liquid or pasty at room temperature and at atmospheric pressure.

Preferably, the fatty substance is a compound that is liquid at a temperature of 25° C. and at atmospheric pressure, or oil.

According to one preferred variant, the fatty substances are not silicone-based.

The fatty substances are preferably chosen from $C_6$-$C_{16}$ hydrocarbons, hydrocarbons comprising more than 16 carbon atoms, non-silicone oils of animal origin, triglycerides of plant or synthetic origin, fatty alcohols, fatty acid and/or fatty alcohol esters, or mixtures thereof.

Preferably, the fatty substance is chosen from linear or branched hydrocarbons, of mineral or synthetic origin, containing more than 16 carbon atoms, or mixtures thereof, for instance liquid petroleum jelly.

The composition in accordance with the invention comprises at least 10% by weight, relative to the total weight of the composition, of fatty substance, preferably of oil, preferably at least 20% by weight, better still at least 30% by weight and even more preferentially at least 40% by weight.

The fatty substance(s) generally represent from 10% to 80% by weight, preferably from 20% to 70%, even more preferentially from 25% to 60% and better still from 35% to 65% by weight relative to the total weight of the composition according to the invention.

Chemical Oxidizing Agent

The composition of the invention comprises one or more chemical oxidizing agents. The term "chemical oxidizing agent" means an oxidizing agent other than atmospheric oxygen.

More particularly, the chemical oxidizing agent(s) are chosen from hydrogen peroxide, urea peroxide, alkali metal bromates, peroxygenated salts, for instance persulfates or perborates, peracids and precursors thereof, and alkali metal or alkaline-earth metal percarbonates.

The oxidizing agent is advantageously hydrogen peroxide.

The concentration of chemical oxidizing agents may range more particularly from 0.1% to 50% by weight, even more preferentially from 3% to 20% by weight and better still from 5% to 15% by weight relative to the weight of the composition.

According to a particular embodiment, the composition in accordance with the invention comprises no dyes or persalts.

The composition according to the invention preferably comprises a cosmetically acceptable medium. For the purposes of the present invention, the term "cosmetically acceptable medium" means a medium that is compatible with keratin materials, in particular keratin fibres, and in particular human keratin fibres such as the hair.

The cosmetically acceptable medium of the composition in accordance with the present invention generally comprises water and/or one or more water-soluble organic solvents. Examples of water-soluble organic solvents that may be mentioned include $C_1$-$C_4$ lower alkanols, such as ethanol and isopropanol; aromatic alcohols such as benzyl alcohol or phenoxyethanol; polyols or polyol ethers such as ethylene glycol monomethyl, monoethyl and monobutyl ether, propylene glycol or ethers thereof such as propylene glycol monomethyl ether, butylene glycol, dipropylene glycol, and also diethylene glycol alkyl ethers, for instance diethylene glycol monomethyl ether or monobutyl ether, or alternatively glycerol; and also mixtures thereof.

The solvents are preferably present in proportions of between 0.1% and 35% by weight approximately, and even more preferentially between 1% and 40% by weight approximately, relative to the total weight of the oxidizing composition.

The composition in accordance with the invention may also comprise additional compounds conventionally used in cosmetics. These compounds may especially be chosen from thickening or stabilizing polymers, non-silicone conditioning polymers, especially cationic non-silicone polymers, chelating agents and fragrances.

According to one embodiment, the composition comprises a polycondensate of ethylene oxide and of propylene oxide of structure (I) below

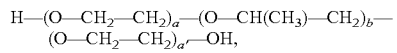

in which a and a' range from 2 to 150 and b ranges from 1 to 100

(polyethylene glycol/polypropylene glycol/polyethylene glycol triblock). In the chemical structure described above, preferably a and a' range from 10 to 130 and b ranges from 20 to 80, better still a and a' range from 50 to 130 and b ranges from 30 to 80 and even better still a and a' range from 80 to 130 and b ranges from 40 to 80. According to a particular embodiment, a and a' are identical.

The polycondensate of ethylene oxide and of propylene oxide that is useful in the composition of the invention preferably has a weight-average molecular weight ranging from 250 to 19 000, better still ranging from 1200 to 15 000, in particular ranging from 1500 to 10 000 and even better still ranging from 1500 to 5000.

Advantageously, the polycondensate of ethylene oxide and propylene oxide has a cloud point, at 10 g/l in distilled water, of greater than or equal to 20° C. and preferably of greater than or equal to 60° C. The cloud point is measured according to standard ISO 1065.

As polycondensates of ethylene oxide and propylene oxide that may be used according to the invention, mention may be made of the polyethylene glycol/polypropylene glycol/polyethylene glycol triblock polycondensates sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184), Synperonic® PE/F88 (INCI name: Poloxamer 238), Synperonic® PE/F87 (INCI name: Poloxamer 237) from the company Croda, or Lutrol® F68 (INCI name: Poloxamer 188) by the company BASF.

According to one embodiment of the invention, the amount of polycondensate(s) of ethylene oxide and propylene oxide preferably ranges from 0.001% to 20% by weight, even more preferentially from 0.01% to 10% by weight and better still from 0.015% to 5% by weight relative to the total weight of the composition. [0.02 g % in Ex. G]

According to another embodiment, the composition according to the invention is free of thickening polymer.

Needless to say, a person skilled in the art will take care to select this or these optional additional compound(s) such that the advantageous properties intrinsically associated with the composition in accordance with the invention are not, or are not substantially, adversely affected by the envisaged addition(s).

The composition according to the invention may be in various forms, such as in the form of a cream, a gel, a milk, a lotion or a mousse, or in any other form that is suitable for treating keratin materials, in particular keratin fibres, and especially human keratin fibres such as the hair. Preferably, it is in the form of a cream or a milk.

The pH of the oxidizing composition according to the invention generally ranges from 1.5 to 4.5 and preferably from 2 to 3.5. It may be adjusted by adding acidifying agents such as hydrochloric acid, acetic acid, lactic acid, boric acid, citric acid or phosphoric acid or acidifying agents in the presence of alkaline agents.

Another subject of the invention is a process for treating keratin materials, in particular keratin fibres, comprising the application to the keratin fibres of an oxidizing composition as defined previously.

The oxidizing composition in accordance with the invention may be used, for example, in a process for dyeing keratin fibres, and in particular human keratin fibres such as the hair.

The process for dyeing keratin fibres in accordance with the invention uses a dye composition comprising, in a support suitable for dyeing keratin fibres, one or more direct dyes and/or one or more oxidation dyes and an oxidizing composition as defined above.

According to this process, the dye composition is applied to the keratin fibres, the colour being revealed, at acidic, neutral or alkaline pH, using an oxidizing composition according to the invention that is applied simultaneously or sequentially, with or without intermediate rinsing.

According to a particularly preferred embodiment of the dyeing process according to the invention, the dye composition is mixed, at the time of use, with an oxidizing composition according to the invention. The mixture obtained is subsequently applied to the keratin fibres and left on for approximately 3 to 50 minutes, preferably approximately 5 to 30 minutes, after which the fibres are rinsed, washed with shampoo, rinsed again and dried.

The direct dye(s) may be chosen from the direct dyes conventionally used in direct dyeing. By way of example, these direct dyes are chosen from nitrobenzene dyes, azo direct dyes, methine direct dyes, quinone direct dyes, azine direct dyes, triarylmethane direct dyes, indoamine direct dyes and natural direct dyes. These direct dyes may be of nonionic, anionic or cationic nature.

Among the benzene-based direct dyes, mention may be made of 1,4-diamino-2-nitrobenzene, 1-amino-2-nitro-4-(β-hydroxyethylamino)benzene, 1-amino-2-nitro-4-bis(β-hydroxyethyl)aminobenzene, 1,4-bis(β-hydroxyethylamino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(6-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(β-hydroxyethylamino)-4-nitrobenzene, 1-amino-2-[tris(hydroxymethyl)methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4, 6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyoxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropyl-amino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis(β-hydroxyethyl)amino]-3-nitrobenzene, 1-β-hydroxyethylamino-2-nitrobenzene and 1-hydroxy-4-β-hydroxyethylamino-3-nitrobenzene.

Among the azo direct dyes, mention may be made of the cationic azo dyes described in patent applications WO 95/15144, WO 95/01772, EP 0 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369 and FR 2 844 269, the content of which forms an integral part of the invention.

Among these compounds, mention may be made most particularly of 1,3-dimethyl-2-[[4-(dimethylamino)phenyl]azo]-1H-imidazolium chloride, 1,3-dimethyl-2-[(4-aminophenyl)azo]-1H-imidazolium chloride and 1-methyl-4-[(methylphenylhydrazono)methyl]pyridinium methyl sulfate.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes, mention may be made of the following compounds: Basic Blue 17, Basic Red 2.

Among the triarylmethane dyes, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes, mention may be made of the following compounds: 2-β-hydroxyethynamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-(3'-chloro-4'-methylamino)phenylureido-6-methyl-1,4-benzoquinoneimine and 3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

The direct dye(s) are generally present in the dye composition in an amount of between 0.001% and 20% by weight approximately and even more preferentially between 0.005% and 10% by weight approximately relative to the total weight of the composition.

The oxidation dye(s) may be chosen from the oxidation bases and couplers conventionally used in the field of dyeing.

Examples of oxidation bases that may be mentioned include para-phenylenediamines, double bases, para-aminophenols, ortho-aminophenols and heterocyclic bases, and the addition salts thereof.

Among the para-phenylenediamines, mention may be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropylpara-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the double bases, examples that may be mentioned include bis(phenyl)alkylenediamines and bis-para-aminophenols.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and 2-[(3-aminopyrazolo[1,5-a]pyridin-2-yl)oxy]ethanol, and the addition salts thereof with an acid or with a base.

Among the pyrimidine derivatives, mention may be made of the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Pyrazole derivatives that may also be mentioned include diamino-N,N-dihydropyrazolopyrazolones and especially those described in patent application FR 2 886 136, such as the following compounds and the addition salts thereof.

Among these compounds, the following are preferred: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Heterocyclic bases that will preferentially be used include 4,5-diamino-1-(β-hydroxyethyl)pyrazole, 2,3-diamino-6,7-dihydro-1H,5H-pyrazolo[1,2-a]pyrazol-1-one and 2-[(3-aminopyrazolo[1,5-a]pyridin-2-yl)oxy]ethanol and/or the addition salts or solvates thereof.

The oxidation base(s) are generally present in the dye composition in an amount of between 0.001% and 10% by weight approximately and preferably between 0.005% and 6% by weight approximately relative to the total weight of the composition.

Examples of couplers that may be mentioned include meta-phenylenediamines, meta-aminophenols, meta-diphenols, naphthalene-based couplers and heterocyclic couplers, and the addition salts thereof.

Mention may be made especially of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

The coupler(s) are generally present in the dye composition in an amount of between 0.001% and 10% by weight approximately and preferably between 0.005% and 6% by weight approximately relative to the total weight of the composition.

In general, the addition salts of the oxidation bases and couplers that may be used in the context of the invention are especially chosen from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The oxidizing composition according to the invention may also be used in a process for bleaching or lightening keratin materials, in particular the skin or keratin fibres, and in particular keratin fibres such as the hair.

The bleaching process according to the invention comprises a step of applying to the keratin materials, in particular the skin or keratin fibres, a bleaching composition preferably comprising aqueous hydrogen peroxide solution in an alkaline medium after mixing at the time of use. Conventionally, a second step of the bleaching process according to the invention is a step of rinsing the keratin materials, in particular keratin fibres.

The bleaching composition applied to the keratin materials, in particular keratin fibres, may be obtained by mixing an oxidizing composition according to the invention with an aqueous or anhydrous composition preferably containing one or more alkaline agents. The anhydrous composition may be pulverulent or in paste form, and in both cases preferably contains one or more peroxygenated salts, and in particular one or more persulfates. The anhydrous composition in paste form also contains one or more inert organic liquids.

In particular, a subject of the invention is a process for dyeing and/or lightening keratin materials, and in particular keratin fibres, more particularly the hair, comprising the application to the keratin materials of a dyeing and/or lightening composition obtained by mixing:
  at least one composition A comprising
    at least one alkaline agent
    optionally at least one colouring agent,
  at least one oxidizing composition as defined previously (known as composition B).

The colouring agent may be chosen from the direct dyes and/or oxidation dyes described above.

The basifying agent(s) may be mineral or organic or hybrid.

The mineral basifying agent(s) are preferably chosen from ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it concerns the $pK_b$ corresponding to the functional group having the highest basicity. In addition, the organic amines do not comprise any alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds having formula (II) below:

in which formula (II) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (II) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (III) below:

in which formula (III) R represents a group chosen from: imidazolyl, preferably 4-imidazolyl; —(CH$_2$)$_3$NH$_2$; —(CH$_2$)$_2$NH$_2$, —(CH$_2$)$_2$—NH—C(O)—NH$_2$; and

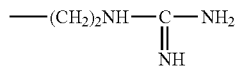

The compounds corresponding to formula (III) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in composition A of the invention are chosen from alkanolamines, amino acids in neutral or ionic form, in particular basic amino acids, and preferably corresponding to those having the formula (III). Even more preferentially, the basifying agent(s) are chosen from monoethanolamine (MEA) and basic amino acids in neutral or ionic form.

Advantageously, composition A according to the invention has a content of basifying agent(s) ranging from 0.01% to 30% by weight and preferably from 0.1% to 20% by weight relative to the weight of composition A.

According to a particular embodiment, composition A or the final composition used in the process according to the invention does not contain ammonia, or a salt thereof, as basifying agent.

Another subject of the present invention is a process for permanently reshaping keratin fibres, and in particular human keratin fibres such as the hair, using an oxidizing composition as defined above.

According to this process, a reducing composition is applied to the keratin fibres to be treated, the keratin fibres being placed under mechanical tension before, during or after the application of the reducing composition, the fibres are optionally rinsed, the oxidizing composition of the present invention is applied to the optionally rinsed fibres, and the fibres are then optionally rinsed again.

The first step of this process consists in applying a reducing composition to the hair. This application is done lock by lock or to the entire head.

The reducing composition comprises at least one reducing agent, which may be chosen in particular from thioglycolic acid, cysteine, cysteamine, glyceryl thioglycolate and thiolactic acid, or thiolactic or thioglycolic acid salts.

The usual step for placing the hair under tension in a shape corresponding to the final shape desired for this hair (for example curls) may be performed by any means, especially mechanical means, which is suitable and known per se for holding the hair under tension, for instance rollers, curlers, combs and the like.

The hair may also be shaped without the aid of external means, simply with the fingers.

Before performing the next optional rinsing step, the head of hair onto which the reducing composition has been applied should conventionally be left to stand for a few minutes, generally between 5 minutes and 1 hour and preferably between 10 and 30 minutes, so as to give the reducing agent enough time to act correctly on the hair. This waiting phase preferably takes place at a temperature ranging from 35° C. to 45° C., while preferably also protecting the hair with a bonnet.

In the second optional rinsing step, the hair impregnated with the reducing composition is rinsed thoroughly with an aqueous composition.

Next, in a third step, the oxidizing composition according to the present invention is applied to the hair thus rinsed, with the aim of fixing the new shape given to the hair.

As in the case of the application of the reducing composition, the head of hair onto which the oxidizing composition has been applied is then, conventionally, left in a standing or waiting phase that lasts a few minutes, generally between 3 and 30 minutes and preferably between 5 and 15 minutes.

If the tension of the hair was maintained by external means, these means (rollers, curlers and the like) may be removed from the head of hair before or after the fixing step.

Lastly, in the final step of the process according to the invention, which is also an optional step, the hair impregnated with the oxidizing composition is rinsed thoroughly, generally with water.

A subject of the present invention is also the use for treating keratin materials, in particular keratin fibres, and in particular human keratin fibres such as the hair, of an oxidizing composition as defined above.

A subject of the present invention is especially the use for dyeing keratin fibres, and in particular human keratin fibres such as the hair, of an oxidizing composition as defined above.

A subject of the present invention is also the use for bleaching or lightening keratin materials, in particular keratin fibres, and in particular human keratin fibres such as the hair, of an oxidizing composition as defined above.

A subject of the present invention is also the use for permanently reshaping keratin fibres, and in particular human keratin fibres such as the hair, of an oxidizing composition as defined above.

The examples that follow illustrate the invention without being limiting in nature.

EXAMPLES

Example 1

The following compositions are prepared:

| Composition (for 100 g) | A (Inv) | B (Inv) | C (comparative) | D (Inv) | E (Inv) | F (Inv) | G (Inv) |
|---|---|---|---|---|---|---|---|
| Hydrogen peroxide as a 50% solution (200 vol. aqueous hydrogen peroxide solution) | 12 | 12 | 12 | 24 | 24 | 24 | 24 |
| Etidronic acid, tetrasodium salt, as an aqueous 30% solution | 0.2 | 0.2 | 0.2 | 0.2 | 0.2 | 0.2 | 0.2 |
| Tetrasodium pyrophosphate decahydrate | 0.04 | 0.04 | 0.04 | 0.04 | 0.04 | 0.04 | 0.04 |
| Sodium salicylate | 0.04 | 0.04 | 0.04 | 0.04 | 0.04 | 0.04 | 0.04 |
| Liquid petroleum jelly | 45 | 45 | 45 | 50 | 50 | 60 | 60 |
| Oxyethylenated stearyl alcohol (2 OE) | 3.5 | 3.75 | 2.5 | 3.5 | 4.9 | 3.5 | 3.5 |
| Oxyethylenated stearyl alcohol (20 OE) | 1.5 | 1.25 | 2.5 | 1.5 | 2.1 | 1.5 | 1.5 |
| Vitamin E | 0.2 | 0.2 | 0.2 | 0.2 | 0.2 | 0.2 | 0.2 |
| Poloxamer 184 Condensate of ethylene oxide and propylene oxide and ethylene oxide (13 EO/30 PO/13 EO) (MW 2900) (INCI: Poloxamer 184) | 0 | 0 | 0 | 0 | 0 | 0 | 0.02 |
| Phosphoric acid | qs pH 2 | qs pH 2 | qs pH 2 | qs pH 2 | qs pH 2 | qs pH 2 | qs pH 2 |
| Water | qs 100 | qs 100 | qs 100 | qs 100 | qs 100 | qs 100 | qs 100 |

They are placed for 2 months at 45° C. and their stability is evaluated visually.

Composition C which has a 2 OE oxyethylenated nonionic surfactant/20 OE oxyethylenated nonionic surfactant weight ratio of 1 is not stable; phase separation takes place a few days after stabilizing the formulation at 45° C.

Compositions A, B, D, E, F and G according to the invention are stable after 2 months at 45° C.

Example 2

The following compositions are prepared (unless otherwise mentioned, the amounts are expressed in g % of product):

Composition (A)

| Chemical name | A1 | A2 |
|---|---|---|
| Aqueous ammonia (20% ammonia reference concentration) | 19.8 | 11.1 |
| Monoethanolamine | 0.63 | 0.63 |
| N-Oleyldihydrosphingosine | 0.01 | 0.01 |
| (Untreated anatase) titanium oxide coated with polydimethylsiloxane (98/2) (CI: 77891) | 0.18 | 0.18 |
| Cetylstearyl alcohol (50/50 C16/C18) | 16.2 | 16.2 |
| Oleyl alcohol | 2.7 | 2.7 |
| Poly[(dimethyliminio)-1,3-propanediyl(dimethyliminio)-1,6-hexanediyl dichloride] as an aqueous 60% solution | 5 | 5 |
| Oleic acid | 2.7 | 2.7 |
| Diethylenetriaminepentaacetic acid, pentasodium salt as an aqueous 40% solution | 2 | 2 |
| Ammonium thiolactate as an aqueous 58% solution (50% thiolactic acid) | 0.8 | 0.8 |
| Oxyethylenated oleocetyl alcohol (30 OE) | 3.6 | 3.6 |
| Water | qs 100 | qs 100 |

Oxidizing Composition (B)

| Chemical name | B2 |
|---|---|
| Mineral oil | 50 |
| Oxyethylenated stearyl alcohol (2 OE) | 3.5 |
| Oxyethylenated stearyl alcohol (20 OE) | 1.5 |
| Vitamin E: | 0.2 |
| Tetrasodium pyrophosphate decahydrate | 0.04 |
| Etidronic acid, tetrasodium salt, as an aqueous 30% solution | 0.2 |
| Sodium salicylate | 0.035 |
| 50% hydrogen peroxide solution | 24 |
| Phosphoric acid | qs pH 2.4 |
| Water | qs 100 |

| Chemical name | B1 |
|---|---|
| 80/20 Cetylstearyl alcohol/oxyethylenated (30 OE) cetylstearyl alcohol mixture | 2.85 |
| Trideceth-2 carboxamide MEA | 0.85 |
| Vitamin E: | 0.2 |
| Tetrasodium pyrophosphate decahydrate | 0.02 |
| Pentasodium pentetate as an aqueous 40% solution | 0.15 |
| Sodium stannate | 0.04 |
| 50% hydrogen peroxide solution | 24 |
| Phosphoric acid | qs pH 2.4 |
| Water | |

At the time of use, the following are mixed together:

1 part by weight of formula A2 with 2 parts by weight of formula B2 (invention)

1 part by weight of formula A1 with 2 parts by weight of formula B1 (comparative)

10 g of each mixture (pH=9.9±0.1) are applied to a 1 g chestnut-brown natural pigmented lock (TD 4). The leave-on time is 50 minutes on a hotplate regulated at 33° C.

After the leave-on time, each lock is rinsed, washed with an iNOA POST shampoo and then left to dry under a hood at 60° C.

The lightening of the locks is evaluated in the CIE L* a* b* system, using a Minolta Spectrophotometer CM2600D colorimeter.

In this L* a* b* system, the three parameters denote, respectively, the intensity (L*), a* indicates the green/red colour axis and b* the blue/yellow colour axis.

The variation in colouring between the locks of 90% grey natural hair that are untreated (control) and after treatment are defined by (ΔE*ab) according to the following equation:

$$\Delta E^* = \sqrt{(a^* - a_o^*)^2 + (b^* - b_o^*)^2}$$

In this equation, L*, a* and b* represent the values measured on locks of hair after dyeing and $L_o^*$, $a_o^*$ and $b_o^*$ represent the values measured on locks of undyed virgin hair. The greater the value of ΔE*, the better the lightening.

Results

|  | L* (D65) | a* (D65) | b* (D65) | ΔE*ab (D65) |
|---|---|---|---|---|
| Untreated hair | 22.06 | 2.95 | 3.52 | — |
| Hair treated with A1 + B1 | 37.56 | 11.33 | 21.21 | 24.96 |
| Hair treated with A2 + B2 | 39.94 | 11.55 | 23.4 | 28.09 |

As shown in the table below, the mixture A2+B2 according to the invention lightens better than the comparative mixture A1+B1. Furthermore, since the composition of the invention comprises 44% less ammonium hydroxide, it gives off a less aggressive ammonia odour.

Example 3

The following compositions were prepared:
Dye Composition

| Chemical name | A3 |
|---|---|
| Aqueous ammonia (20% ammonia reference concentration) | 11.1 |
| Monoethanolamine | 0.63 |
| N-Oleyldihydrosphingosine | 0.01 |
| Cetylstearyl alcohol (50/50 C16/C18) | 16.2 |
| Oleyl alcohol | 2.7 |
| Poly[(dimethyliminio)-1,3-propanediyl(dimethyliminio)-1,6-hexanediyl dichloride] as an aqueous 60% solution | 5 |
| Oleic acid | 2.7 |
| Diethylenetriaminepentaacetic acid, pentasodium salt as an aqueous 40% solution | 2 |
| Ammonium thiolactate as an aqueous 58% solution (50% thiolactic acid) | 0.54 |
| Oxyethylenated (30 OE) oleocetyl alcohol | 3.6 |
| 1-Methyl-2,5-diaminobenzene | 0.06 |
| 1-Hydroxy-4-aminobenzene | 0.0085 |
| N,N-Bis(2-hydroxyethyl)-p-phenylenediamine sulfate monohydrate | 0.01 |
| 1,3-Dihydroxybenzene (resorcinol) | 0.07 |
| 1-Hydroxy-3-aminobenzene | 0.006 |
| 1-Beta-hydroxyethyloxy-2,4-diaminobenzene dihydrochloride | 0.003 |
| Deionized water | qs 100 |

The oxidizing agent B2 described above is used.

At the time of use, 1 part by weight of formula A3 is mixed with 2 parts by weight of formula B2.

10 g of the mixture (pH=9.8) are applied to a 1 g light chestnut-brown natural pigmented lock (TD 8). The leave-on time is 50 minutes on a hotplate regulated at 33° C.

After the leave-on time, each lock is rinsed, washed with an iNOA POST shampoo and then left to dry under a hood at 60° C.

The colouring of the lock is evaluated in the CIE L* a* b* system, using a Minolta Spectrophotometer CM2600D colorimeter.

A luminous golden-blonde colour is obtained.

|  | L* (D65) | a* (D65) | b* (D65) | ΔE*ab (D65) |
|---|---|---|---|---|
| Untreated hair | 43.32 | 7.71 | 18.71 | — |
| Hair treated with A3 + B2 | 57.62 | 6.21 | 23.23 | 15.06 |

The invention claimed is:

1. A composition for treating keratin materials, the composition comprising, in a cosmetically acceptable medium:
    at least one fatty substance, present in an amount greater than or equal to about 10% by weight, relative to the total weight of the composition,
    at least one oxyalkylenated (OA) nonionic surfactant comprising from 1 to 9 OA units, chosen from saturated or unsaturated, linear or branched oxyethylenated $C_8$-$C_{30}$ fatty alcohols,
    at least one oxyalkylenated (OA) nonionic surfactant comprising at least 10 OA units, and
    at least one chemical oxidizing agent,
    wherein the weight ratio of the amount of the at least one oxyalkylenated nonionic surfactant comprising from 1 to 9 OA units to the amount of the at least one oxyalkylenated nonionic surfactant comprising at least 10 OA units, is greater than 1,
    wherein the composition comprises no hair dye,
    wherein the composition is stable for at least two months at 45° C., and
    wherein the composition is an oxidizing composition.

2. The composition of claim 1, wherein the at least one oxyalkylenated nonionic surfactant comprising at least 10 OA units, and the at least one oxyalkylenated nonionic surfactant comprising from 1 to 9 OA units, are chosen from saturated or unsaturated, linear or branched $C_{12}$-$C_{22}$ oxyethylenated fatty alcohols.

3. The composition of claim 1, wherein the at least one oxyalkylenated nonionic surfactant comprising at least 10 OA units, and the oxyalkylenated nonionic surfactant comprising from 1 to 9 OA units, are chosen from $C_{14}$-$C_{20}$ oxyethylenated fatty alcohols.

4. The composition of claim 1, wherein the at least one oxyalkylenated nonionic surfactant comprising at least 10 OA units, comprises from 10 to 50 oxyalkylene groups.

5. The composition of claim 1, wherein the at least one oxyalkylenated nonionic surfactant comprising at least 10 OA units is Steareth-20.

6. The composition of claim 1, wherein the at least one oxyalkylenated nonionic surfactant comprising from 1 to 9 OA units, comprises from 2 to 8 oxyethylenated (OE) units.

7. The composition of claim 1, wherein the at least one oxyalkylenated nonionic surfactant comprising from 1 to 9 OA units is Steareth-2.

8. The composition of claim 1, wherein the at least one oxyalkylenated nonionic surfactant comprising at least 10 OA units is present in an amount ranging from about 0.1% to about 20% by weight, relative to the total weight of the composition.

9. The composition of claim 1, wherein the at least one oxyalkylenated nonionic surfactant comprising from 1 to 9

OA units is present in an amount ranging from about 0.5% to about 15% by weight, relative to the total weight of the composition.

10. The composition of claim 1, wherein the at least one oxyalkylenated nonionic surfactant comprising at least 10 oxyalkylene groups is present in an amount ranging from about 0.1% to about 15% by weight, relative to the total weight of the composition.

11. The composition of claim 1, wherein the at least one fatty substance is chosen from compounds that are liquid at a temperature of 25° C. and at atmospheric pressure, or oil.

12. The composition of claim 1, wherein the at least one fatty substance is chosen from $C_6$-$C_{16}$ hydrocarbons, hydrocarbons comprising more than 16 carbon atoms, non-silicone oils of animal origin, triglycerides of plant or synthetic origin, fatty alcohols, fatty acid esters, fatty alcohol esters, or mixtures thereof.

13. The composition of claim 1, wherein the at least one fatty substance is chosen from linear or branched hydrocarbons, of mineral or synthetic origin, containing more than 16 carbon atoms.

14. The composition of claim 1, wherein the at least one fatty substance is present in an amount greater than or equal to about 20% by weight, relative to the total weight of the composition.

15. The composition of claim 1, wherein the at least one chemical oxidizing agent is hydrogen peroxide.

16. The composition of claim 1, wherein the at least one chemical oxidizing agent is present in an amount ranging from about 1% to about 50% by weight, relative to the total weight of the composition.

17. A method for treating keratin materials, comprising applying to the keratin materials an oxidizing composition, the oxidizing composition comprising:
  at least one fatty substance, present in an amount greater than or equal to about 10% by weight, relative to the total weight of the composition,
  at least one oxyalkylenated (OA) nonionic surfactant comprising from 1 to 9 OA units, chosen from saturated or unsaturated, linear or branched oxyethylenated $C_8$-$C_{30}$ fatty alcohols,
  at least one oxyalkylenated (OA) nonionic surfactant comprising at least 10 OA units, and
  at least one chemical oxidizing agent,
  wherein the weight ratio of the amount of the at least one oxyalkylenated nonionic surfactant comprising from 1 to 9 OA units to the amount of the at least one oxyalkylenated nonionic surfactant comprising at least 10 OA units, is greater than 1,
  wherein the composition comprises no hair dye, and
  wherein the composition is stable for at least two months at 45° C.

18. A method for dyeing and/or lightening keratin materials, comprising applying to the keratin materials a dyeing and/or lightening composition obtained by mixing:
  a) at least one composition A comprising:
    at least one alkaline agent,
    optionally at least one colouring agent, and
  b) at least one composition B comprising:
    at least one fatty substance, present in an amount greater than or equal to about 10% by weight, relative to the total weight of the composition,
    at least one oxyalkylenated (OA) nonionic surfactant comprising from 1 to 9 OA units, chosen from saturated or unsaturated, linear or branched oxyethylenated $C_8$-$C_{30}$ fatty alcohols,
    at least one oxyalkylenated (OA) nonionic surfactant comprising at least 10 OA units, and
    at least one chemical oxidizing agent,
    wherein the weight ratio of the amount of the at least one oxyalkylenated nonionic surfactant comprising from 1 to 9 OA units to the amount of the at least one oxyalkylenated nonionic surfactant comprising at least 10 OA units, is greater than 1,
    wherein the composition B comprises no hair dye,
    wherein the composition B is stable for at least two months at 45° C., and
    wherein the composition B is an oxidation composition.

19. The method of claim 18, wherein the at least one alkaline agent is chosen from aqueous ammonia, alkali metal carbonates, alkali metal bicarbonates, organic amines chosen from alkanolamines, oxyethylenated ethylenediamines, oxypropylenated ethylenediamines, amino acids, compounds of formula (II) below, or mixtures thereof:

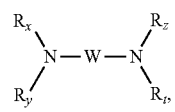

(II)

wherein W is chosen from a divalent $C_1$-$C_6$ alkylene radical optionally substituted with at least one hydroxyl group or a $C_1$-$C_6$ alkyl radical, and/or optionally interrupted with at least one heteroatoms, or $NR_u$; $R_x$, $R_y$, $R_z$, $R_t$, and $R_u$, which may be identical or different, are chosen from a hydrogen atom, a $C_1$-$C_6$ alkyl radical, a $C_1$-$C_6$ hydroxyalkyl radical, a $C_1$-$C_6$ aminoalkyl radical, amino acids in neutral form, or amino acids in ionic form.

20. The method of claim 18, wherein composition A further comprises at least one coloring agent chosen from oxidation dye precursors, direct dyes, or mixtures thereof.

* * * * *